United States Patent
Hicks et al.

(10) Patent No.: US 6,346,121 B1
(45) Date of Patent: Feb. 12, 2002

(54) OCULAR SOCKET PROSTHESIS

(75) Inventors: Celia Hicks, Carlisle; Anthony Clayton, Malvern East; Traian Chirila, Bentley; Geoffrey Crawford, Floreat; Ian Constable, Mosman Park; Janet Fitton, Sandy Bay, all of (AU)

(73) Assignee: The Lions Eye Institute of Western Australia Incorporated, Nedlands (AU)

( * ) Notice: Subject to any disclaimer, the term of this patent is extended or adjusted under 35 U.S.C. 154(b) by 0 days.

(21) Appl. No.: 09/242,896
(22) PCT Filed: Aug. 14, 1997
(86) PCT No.: PCT/AU97/00512
  § 371 Date: Nov. 22, 1999
  § 102(e) Date: Nov. 22, 1999
(87) PCT Pub. No.: WO98/08549
  PCT Pub. Date: May 5, 1998

(30) Foreign Application Priority Data

Aug. 26, 1996 (AU) .................................. PO 1857

(51) Int. Cl.⁷ .................................................. A61F 2/16
(52) U.S. Cl. ........................................ 623/6.64; 623/4.1
(58) Field of Search ................................ 623/4.1, 6.64, 623/5.11

(56) References Cited

U.S. PATENT DOCUMENTS

| | | | |
|---|---|---|---|
| 4,889,530 A | * 12/1989 | Smith et al. | ................. 604/304 |
| 5,192,315 A | 3/1993 | Jacob-LaBarre | |
| 5,584,880 A | * 12/1996 | Martinez | ................... 623/6.64 |
| 5,834,007 A | * 11/1998 | Kubota | ........................ 424/443 |

FOREIGN PATENT DOCUMENTS

| | | | |
|---|---|---|---|
| AU | 20824/92 | | 2/1994 |
| FR | 2 698 264 | | 5/1994 |
| GB | 2150938 | * | 7/1985 |

OTHER PUBLICATIONS

Patent abstract of Japanese Application No. 06–142183, published May 24, 1994.

* cited by examiner

*Primary Examiner*—Corrine McDermott
*Assistant Examiner*—Brian E Pellegrino
(74) *Attorney, Agent, or Firm*—Browdy and Neimark

(57) ABSTRACT

The invention provides an ocular socket prosthesis comprising a hydrogel consisting essentially of a biocompatible hydrophilic polymer onto which tissues can be directly sutured. Preferably the prosthesis comprises the polymer both in its homogeneous gel form and in its sponge form, and the two forms are chemically joined at their interface via an interpenetrating polymer network (IPN). However, it is also contemplated that the prosthesis of the invention may be made predominantly or entirely from the sponge form of the polymer. Methods of production of the prosthesis of the invention and of surgical implantation are also disclosed and claimed.

14 Claims, 7 Drawing Sheets

OCULAR SOCKET PROSTHESIS

This invention relates to ocular prostheses, and in particular to prosthetic replacements for the eyeball. In one embodiment, the invention provides an eyeball prosthesis of an improved material.

BACKGROUND OF THE INVENTION

It is common for an eye to have to be removed because of severe trauma, infection, congenital abnormality, untreatable painful glaucoma, or the presence of a tumour. After removal of an eye it is desirable to place a prosthetic globe of similar volume within the eye socket cavity. If this is not done in children the orbit orbital bones fail to develop normally, making wearing of a cosmetic shell difficult, and resulting in an unsightly appearance (Soll, 1982; Kennedy, 1973; Berry, 1991). In an adult, although volume replacement is not necessary in terms of bone development, which is already complete, it is vital for orbital volume to be maintained if the patient is to be fitted with an external cosmetic shell and to obtain a natural appearance and "eye" movement. A prosthesis is required for similar reasons if an eye is congenitally absent. Thus there is a widespread need for eyeball prostheses (socket prostheses).

The usual procedure on removal of an eye is to dissect off and preserve the covering conjunctiva, Tenon's capsule (a thicker connective tissue layer which forms the fascial sheath of the eyeball) and the muscles responsible for eye movement. A prosthetic globe is then pushed into the space, the muscles are attached to the prosthesis, and covering tissues are sutured over the outside (Nunery et al, 1993). Once the tissues have healed, an external cosmetic shell can be worn over this surface under the eyelids, and should give reasonable cosmesis and some movement, as it is "carried" by movement of the implanted prosthesis. However, although,in principle an effective prosthesis is possible, major technical difficulties remain to be overcome.

The criteria for an ideal ocular prosthesis are simple; it should be buried in the existing eye socket, and it should be simple, light, smooth and inert (Soll, 1982). In particular, such an ideal prosthesis will not provoke any inflammatory response, and will permit suturing of the ocular muscles directly to the prosthesis so as to provide movement simulating that of the patient's own eye.

It is clear from the literature that the ideal orbital implant has not yet been achieved. Mules appears to have been the first surgeon to place a hollow glass sphere, which he called "artificial vitreous", within the scleral cavity of an eviscerated eye in human patients with the aim of improving cosmesis; infection-related extrusion was the greatest problem experienced (Mules, 1884). Lang and Frost both developed this idea by using a glass ball as a volume replacement after enucleation; Lang subsequently used celluloid balls to avoid the risk of breakage of a glass prosthesis (Lang, 1887).

Jardon (U.S. Pat. No. 2,688,139) proposed a ball with irregular surface and perforations to encourage tissue ingrowth. Polytetrafluoroethylene, polyethylene, poly (methyl methacrylate) and nylon were suggested as materials.

In recent years simple poly(methyl methacrylate) or silicone spheres have become the norm, in spite of extrusion rates of over 10% in some series (Nunery, 1993). However, it is impossible to attach muscles directly to these materials. Therefore the implant must first be covered with donor cadaveric sclera or with a synthetic material such as Dacron (trade mark), and the muscles are then sutured to the covering layer.

Recently prostheses made of hydroxyapatite have been used in some centres (Perry, U.S. Pat. No. 4,976,731; Dutton, 1991), and these are thought to give a better outcome because, since hydroxyapatite is porous, the surrounding tissues can grow into the ball and help to secure it. However, hydroxyapatite is a hard material and cannot be sutured directly to the tissues; therefore it must still be covered with sclera or Dacron. Furthermore, hydroxyapatite implants are extremely expensive (Dutton, 1991; McNab, 1995) and are thus not routinely available to patients even in many economically developed countries.

Hydroxyapatite implants have gained in popularity in those countries where they are affordable, and several large series have been reported (Dutton, 1991; Shields et al, 1993; Shields, 1992; Shields, 1994). There is evidence that fibrovascular ingrowth into hydroxyapatite does take place, although it appears to be accompanied by a degree of inflammation of the foreign body type (McNab, 1995; Shields et al, 1991; Rosner et al, 1992; Rubin et al, 1994). Moreover, extrusion of the prosthesis can still occur (McNab, 1995; Buettner and Bartley, 1992).

Rubin et al (1994) reported a study in rabbits, in which spheres of hydroxyapatite, 14 mm in diameter, were compared with spheres of porous polyethylene. Vascularisation occurred more quickly in the hydroxyapatite spheres, especially near to the muscle insertions, but both materials showed a low-grade foreign body response.

Girard (1990) has proposed Proplast (trade mark) as both an enucleation implant, citing Neuhaus (1984), and as an evisceration implant, and describes his evisceration technique in the pig in 4 eyes with a maximum of 1.5 years follow-up. This work appears promising, but the results of more extensive trials are awaited. Some studies of keratoprosthesis development have found Proplast to be prone to an inflammatory response and resultant extrusion from the eye (Legeais et al, 1992).

Vachet (U.S. Pat. No. 5,089,021) proposed a ball silicone elastomer covered with porous polytetrafluoroethylene. The porous material is not incorporated into the ball, and is attached either by suturing (like covering a wooden cricket ball with leather) or by adhesives.

Jacob-LaBarre (U.S. Pat. No. 5,192,315) proposed a silicone ball covered with "patches" of porous silicone (for cellular ingrowth) and other porous polymers (for muscle attachment) such as polyurethanes, polyesters, or polytetrafluoroethylene. The means by which the patches are adjoined to the underlying prostheses is not explained. Bare areas between patches are said to enhance mobility by preventing too much tissue attachment.

Goldberg et al (1994) have proposed using porous polyethylene implants which, like Proplast, do not require wrapping, and which allow muscles to be sutured directly to the implant. They reported trying the material in 16 rabbits; there were 2 early extrusions related to infection. Hydroxyapatite spheres used for comparison in 2 rabbits seemed to provoke more inflammation, but fibrous encapsulation occurred with both. The polyethylene showed fibrovascular ingrowth and macrophage invasion; however, the fibrovascular tissue did not reach the centre of the sphere.

De-epithelialized dermal fat grafts have also been used as primary as well as secondary orbital implants (Smith and Petrelli, 1978; Migliori and Putterman, 1991; Smith et al, 1988; Borodic et al, 1989); however, resorption of the fat may occur. Buccal mucous membrane grafts are of use in the contracted socket as a secondary procedure, providing both volume and mucosal surface (Molget et al, 1993). Unless autografts are employed, such fat or mucous membrane graft would entail a risk of graft rejection, as well as a high risk of disease transmission.

Currently the globe prostheses used are generally made of silicone (Nunery et al, 1993; Soll, 1974; Nunery, 1993) in a range of sizes. These prostheses themselves cannot integrate with tissues, or have muscles directly attached to them. They therefore have to be covered before implantation with either donor sclera from a cadaver (Soll, 1974), or with Dacron (trade mark) mesh. Dacron is expensive, and often fails to prevent extrusion, possibly because it does not cushion the prosthesis in any way; if the covering tissues are thin or weak the prosthesis may erode through them. Once such erosion has occurred re-implantation is technically very difficult, and cosmetic appearance and movement are often unsatisfactory. The use of cadaver tissue is undesirable because of the high risk of disease transmission and because of the chronic shortage of donor tissue.

Thus it can be seen that the prosthetic materials and techniques available in the prior art still suffer from problems of:

infection;

inflammation due to foreign body response;

poor attachment of extraocular muscles;

poor integration with surrounding tissues;

erosion of covering tissues;

extrusion of the prosthesis;

expense of certain materials; and high risk of transmission of disease such as HIV, hepatitis virus and Creutzfeld-Jacob disease when transplanted cadaver tissues are used.

Previous work carried out in the applicant's laboratory has shown that a particular hydrophilic polymer has considerable advantages in the manufacture of a composite corneal prosthesis (keratoprosthesis). The polymerisation characteristics of this polymer enabled production of a prosthesis having an annular opaque, spongy peripheral zone surrounding a central, transparent optic zone, in which the two zones were joined by an interpenetrating polymer network. The surrounding tissues were able to invade the spongy peripheral zone following implantation (Australian Patent No. 650156, equivalent to U.S. Pat. No. 5,458,819, and Chirila et al, 1994). Because of the functional requirements of the cornea, it was essential that the polymer used for the centre of the keratoprosthesis be capable of being transparent.

We have now surprisingly found that a hydrogel comprising a biocompatible hydrophilic polymer such as poly (2-hydroxyethyl methacrylate) can be used to form a socket prosthesis of novel construction. The physical and chemical properties of this material provide a number of significant advantages.

SUMMARY OF THE INVENTION

According to a first aspect, the invention provides an ocular socket prosthesis comprising a hydrogel consisting essentially of a biocompatible hydrophilic polymer on to which tissues can be directly sutured.

Preferably the prosthesis comprises the polymer both in its homogeneous gel form and in its sponge form, and the two forms are chemically joined at their interface via an interpenetrating polymer network (IPN). However, it is also contemplated that the prosthesis of the invention may be made predominantly or entirely from the sponge form of the polymer.

In one preferred embodiment, the prosthesis is generally spherical, and comprises a posterior hemisphere consisting essentially of the gel form of the polymer and an anterior hemisphere consisting essentially of the sponge form of the polymer, said anterior and posterior hemispheres being permanently joined at their interface by an IPN.

Optionally the anterior hemisphere is strengthened by a column of the gel form of the polymer, which extends from the surface of the anterior hemisphere towards the centre of the prosthesis; the gel column may extend to meet the posterior hemisphere, but need not do so.

In an alternative preferred embodiment, the prosthesis is generally spherical, and comprises two generally concentric regions, with a generally spherical central core consisting essentially of the homogeneous gel form of the polymer surrounded by a layer of the sponge form of the polymer, the core and the outer layer being permanently joined by an IPN.

It will be clearly understood that other means of attachment between the gel and sponge components of the prosthesis are within the scope of the invention; for example, a variety of suitable adhesives acceptable for surgical use will be known to the person skilled in the art. However, it is considered that the permanent joining of the preferred embodiments of the invention provides a significant advantage.

In both embodiments, the anterior surface of the prosthesis may optionally carry connecting means adapted to cooperate with corresponding receiving means on an externally-worn cosmetic shell. For example the prosthesis may have an anterior point, nipple, hole or groove adapted to interlock with a corresponding means in the cosmetic shell. It is considered that this would be safer than breaching the conjunctival covering tissue by placing a peg into the prosthesis in order to couple the prosthesis to the shell, as has been used in conjunction with hydroxyapatite implants (Shields et al, 1993).

In the prosthesis of the invention, the solid gel form of the polymer and the sponge form of the polymer are permanently chemically joined at their interface via a tight attachment which is achieved by the penetration of the hydrophilic monomer solution into the pores of the polymer sponge. Thus a sequential IPN is formed by penetration of the monomer through diffusion into the substance of the sponge, ie. by swelling. To some extent the solid gel is polymerised on the matrices of the sponge. Thus the prosthesis is produced by a sequential two-stage polymerisation performed in the same mould, in which the hydrogel sponge portion is formed first; during the second stage the monomer mixture firstly penetrates to some extent into the pre-existing polymer matrix and subsequently undergoes polymerisation, so as to form an interpenetrating polymer network along the boundary between the two portions.

Any biocompatible hydrophilic polymer capable of forming both a gel form and a spongy form of the polymer will be suitable for use in the invention. However, we have found that poly(2-hydroxyethyl methacrylate) (PHEMA) is particularly suitable for the purposes of the invention. The monomer, 2-hydroxyethyl methacrylate (HEMA), would normally be used at a concentration of 5 to 25% by weight in water. A cross-linking agent (0.2% to 1% by weight, based on the total amount of monomer) and a water-soluble initiator (0.05% to 1% by weight, based on the total amount of monomer) is added in order to effect polymerisation.

Optionally other monomers may be used in conjunction with HEMA to form a copolymer. These may be hydrophilic or hydrophobic monomers, and include for example other hydroxylated methacrylates and acrylates, acrylamide derivatives and N-vinylpyrrolidone and combinations thereof; hydrophobic methacrylates and acrylates; and other hydrophobic monomers. The person skilled in the art would be aware of many suitable comonomers. For example, a number of suitable compounds are described in our earlier Australian Patent No. 650156. This earlier patent also discusses in detail methods for production of the polymers. However, the person skilled in the art will appreciate that for the purposes of the present invention it is not necessary that any part of the prosthesis be transparent.

In selecting an appropriate material for the prosthesis of the invention, it must be borne in mind that the prosthesis must be capable of being sterilised, preferably by autoclaving at 120° for 20 minutes. The prosthesis will normally be stored in sterile solution, such as phosphate buffered saline, until implantation.

The prosthesis of the invention may optionally be impregnated with collagen prior to implantation, in order to stimulate cellular ingrowth from the surrounding tissues. For example, the sterilised prosthesis is incubated for 18 to 24 hours at 4° in an aqueous solution of sterile collagen (1.35 mg/ml) at pH 7.4, then warmed to 37° and incubated for 1 hour before being transferred into sterile phosphate buffered saline for storage prior to implantation.

In order to reduce the risk of infection, the prosthesis may also be soaked in antibiotic solution before implantation.

Other optional treatments before implantation, for example to modify the tissue response, are also within the scope of the invention.

DETAILED DESCRIPTION OF THE INVENTION

The invention will now be described in detail by way of example only with reference to the examples and to the figures, in which.

Figure 1A:
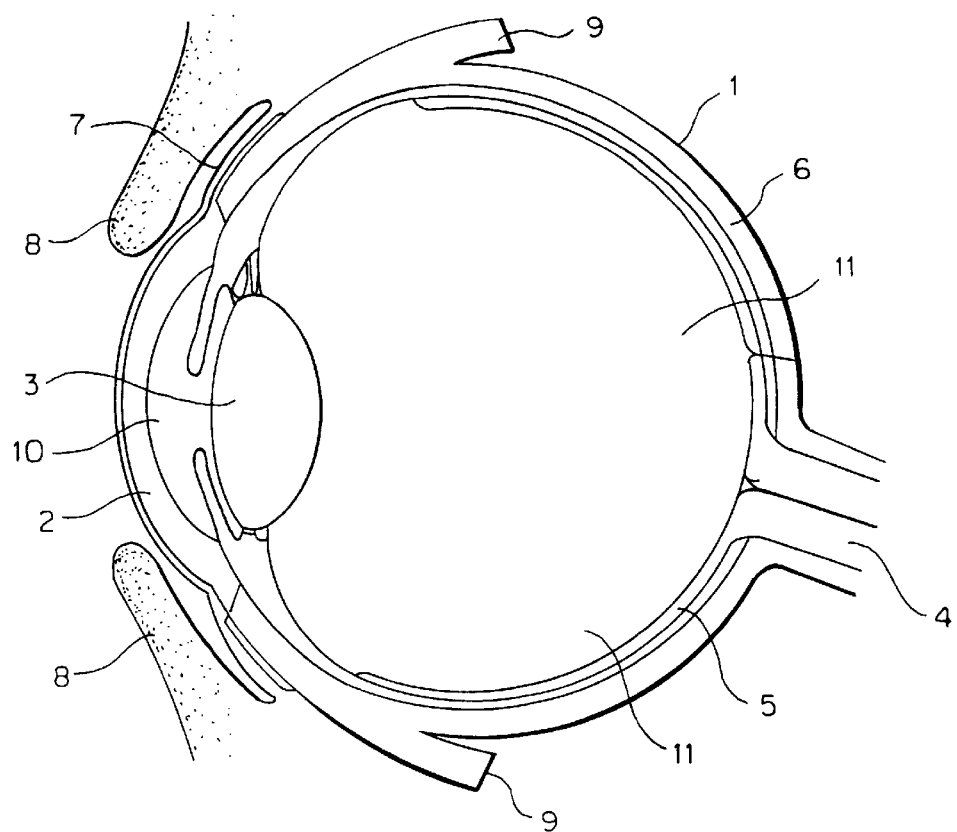
FIG. 1a represents a sagittal section showing the eyeball and surrounding tissues.

The eyeball and surrounding structures are generally illustrated in FIG. 1a, which represents a sagittal section through the eyeball. Only the principal structures relevant to the present invention are shown. The eyeball (1) is bounded anteriorly by the cornea (2), and is separated into anterior and posterior portions by the lens (3). The optic nerve (4) carries visual impulses from the retina (5) to the brain. The posterior portion of the eyeball is surrounded by the sclera (6) and Tenon's capsule connective tissue (not shown), and the cornea (2) is covered by an epithelium which is continuous with the conjunctive (7), which is in turn continuous with the lining of the eyelids (8). Movement of the eyeball is controlled by the extrinsic muscles (9), of which only two are shown in this figure. The anterior chamber of the eye between the cornea and the lens is filled with a watery fluid, the aqueous humour (10), while the posterior chamber behind the lens is filled with the vitreous humour (vitreous body) (11), which is a transparent gel-like material.

Figure 1B:
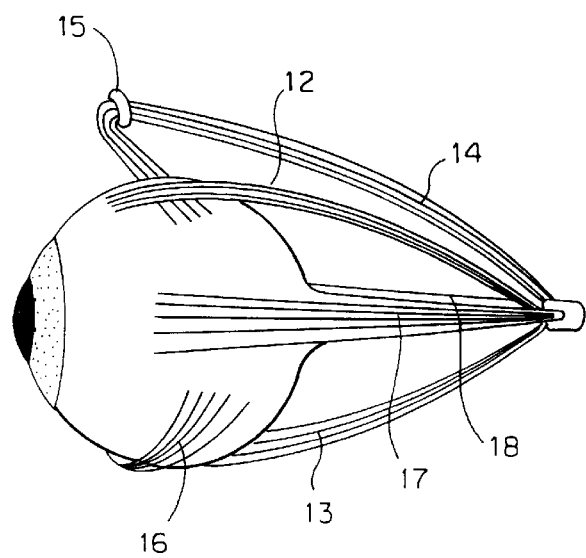
FIG. 1b illustrates the extrinsic muscles which control eye movement, and their attachments to the eyeball.

The movements of the eyeball are controlled by three pairs of extrinsic eye muscles, which are illustrated in FIG. 1b. These are the superior rectus muscle (12) the inferior rectus muscle (13); the superior oblique muscle (14), which is bent about a pulley (15), and the inferior oblique muscle (16); and the lateral rectus muscle (17) and the medial rectus muscle (18). The pulley or trochlea is a fibrous loop in the orbital cavity, located near the nasal process of the frontal bone, through which the tendon of the superior oblique muscle passes.

EXAMPLE 1

Figure 2:
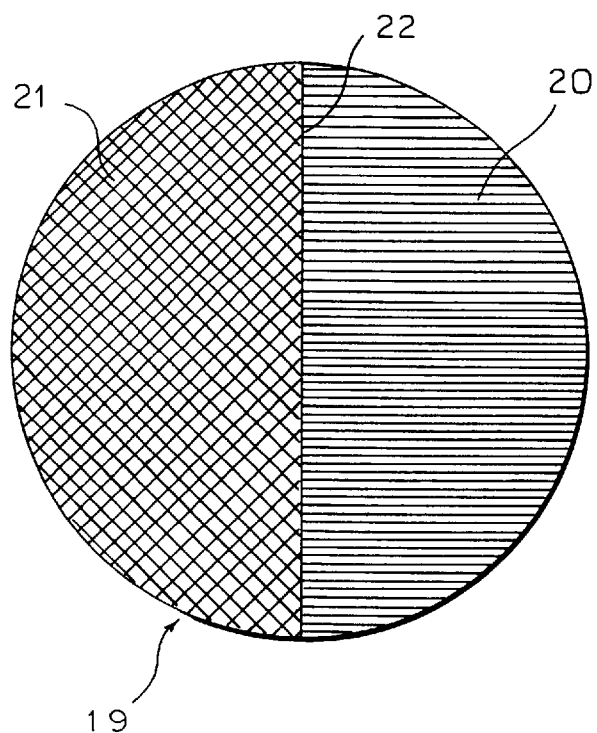
FIG. 2 illustrates a sagittal section of a first preferred embodiment of the invention, in which the prosthesis comprises a homogeneous gel hemisphere and a sponge hemisphere.

A first preferred embodiment of the invention is illustrated in FIG. 2. This shows a socket prosthesis (19), which is generally spherical in shape, and which comprises an anterior hemisphere (20) which consists of PHEMA in its sponge form, and a posterior hemisphere (21) which consists of the PHEMA polymer in its homogeneous gel form. The interface (22) between the two hemispheres constitutes an interpenetrating polymer network, which provides a permanent chemical attachment between the two hemispheres. In this embodiment the ocular extrinsic muscles are sutured directly into the sponge, so that a covering layer of sclera or Dacron is not required. The fascial sheath of the eyeball (Tenon's capsule) and the conjunctiva are closed over the outside of the prosthesis. The spongy consistency of the anterior hemisphere permits cell ingrowth from the extrinsic muscles and from connective tissues. In contrast, the smooth surface of the solid polymer gel which forms the posterior hemisphere prevents direct tissue integration into the polymer, and therefore maximises the range of movement of the prosthesis.

EXAMPLE 2

Figure 3:
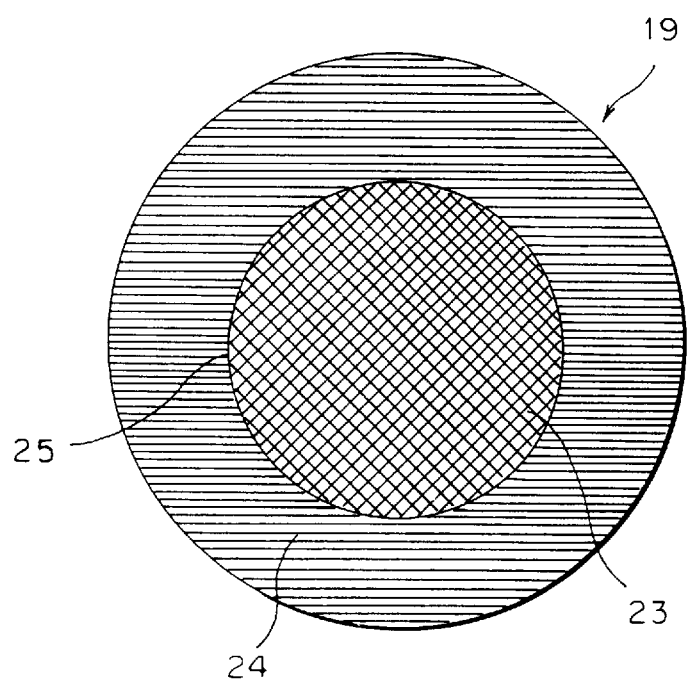
FIG. 3 illustrates a sagittal section of a second preferred embodiment of the invention, in which a homogeneous gel core is surrounded by a layer of sponge polymer.

A second preferred embodiment of the invention is illustrated in FIG. 3. The prosthesis (19) is again generally spherical, but in this case consists of a homogeneous gel core (23) surrounded by a sponge layer (24). Again the interface (25) between the core (23) and the outer layer (24) is an interpenetrating polymer network, providing a permanent chemical attachment between the two. It can be seen that in this embodiment the whole surface of the prosthesis is provided by the spongy polymer, and therefore tissue integration can take place over the entire surface. This will minimise the risk of extrusion of the prosthesis, but may not allow as much movement as in the first embodiment.

Figure 4:
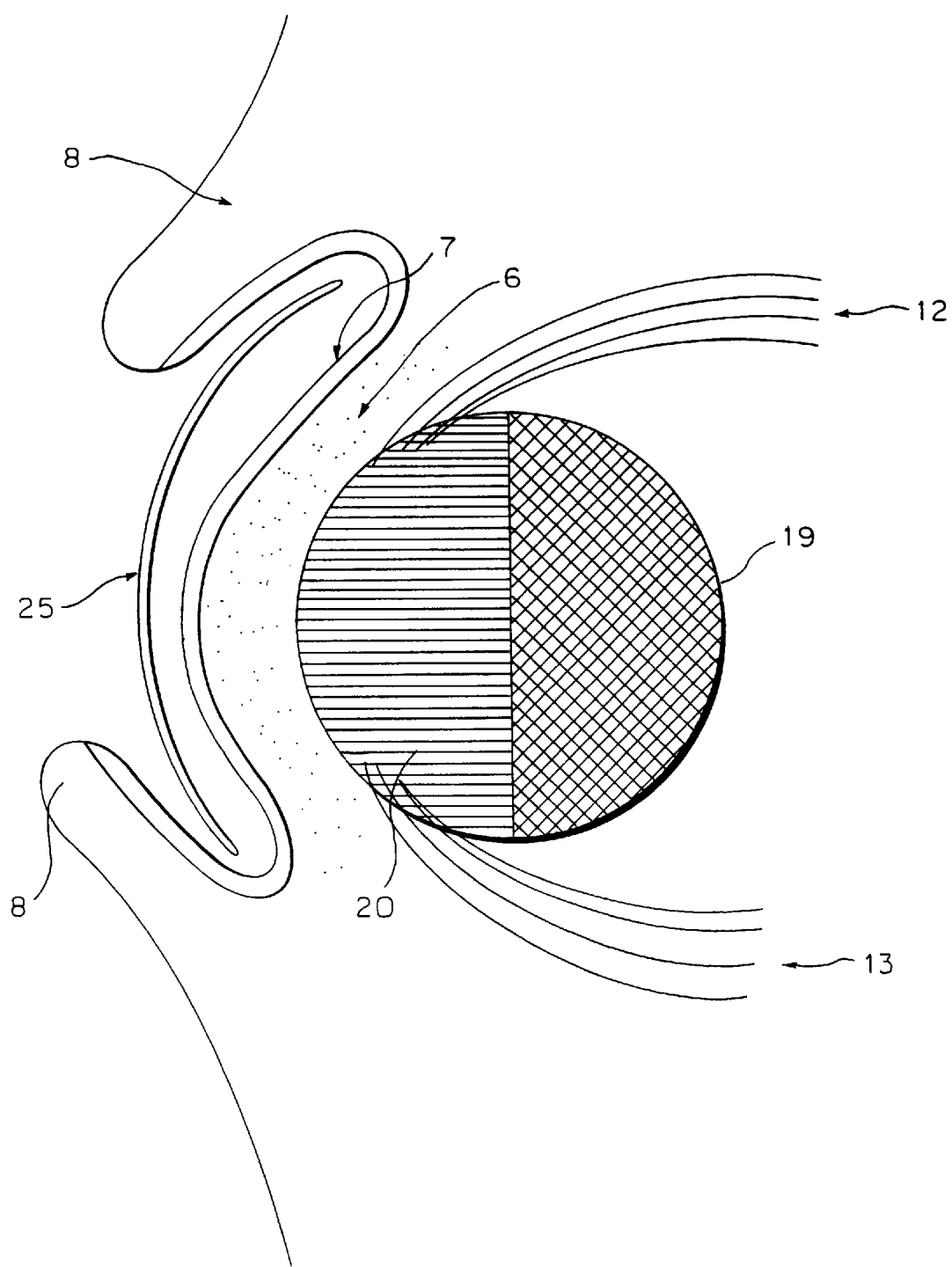
FIG. 4 illustrates a sagittal section showing a prosthesis according to the first embodiment of the invention in situ after implantation.

FIG. 4 is a sagittal section showing a prosthesis according to the first embodiment of the invention in situ after implantation. The prosthesis (19) lies under the sutured conjunctiva (7). The extraocular muscles, of which only the superior rectus (12) and the inferior rectus (13) are shown, and the Tenon's capsule connective tissue (6) are attached to and integrating with the anterior hemisphere (20) of the prosthesis (19). The externally-worn cosmetic shell (25) lies under the eyelids (8), which hold the cosmetic shell (25) in position.

EXAMPLE 3

A third preferred embodiment of the invention is illustrated in FIG. 4. As in the first two embodiments, the prosthesis (19) is again generally spherical, and as in the first embodiment comprises an anterior hemisphere (20) which consists of PHEMA in its sponge form, and a posterior hemisphere (21) which consists of PHEMA polymer in its homogeneous gel form. Again the interface (22) between the two hemispheres constitutes a interpenetrating polymer network as described in Example 1.

Figure 5:
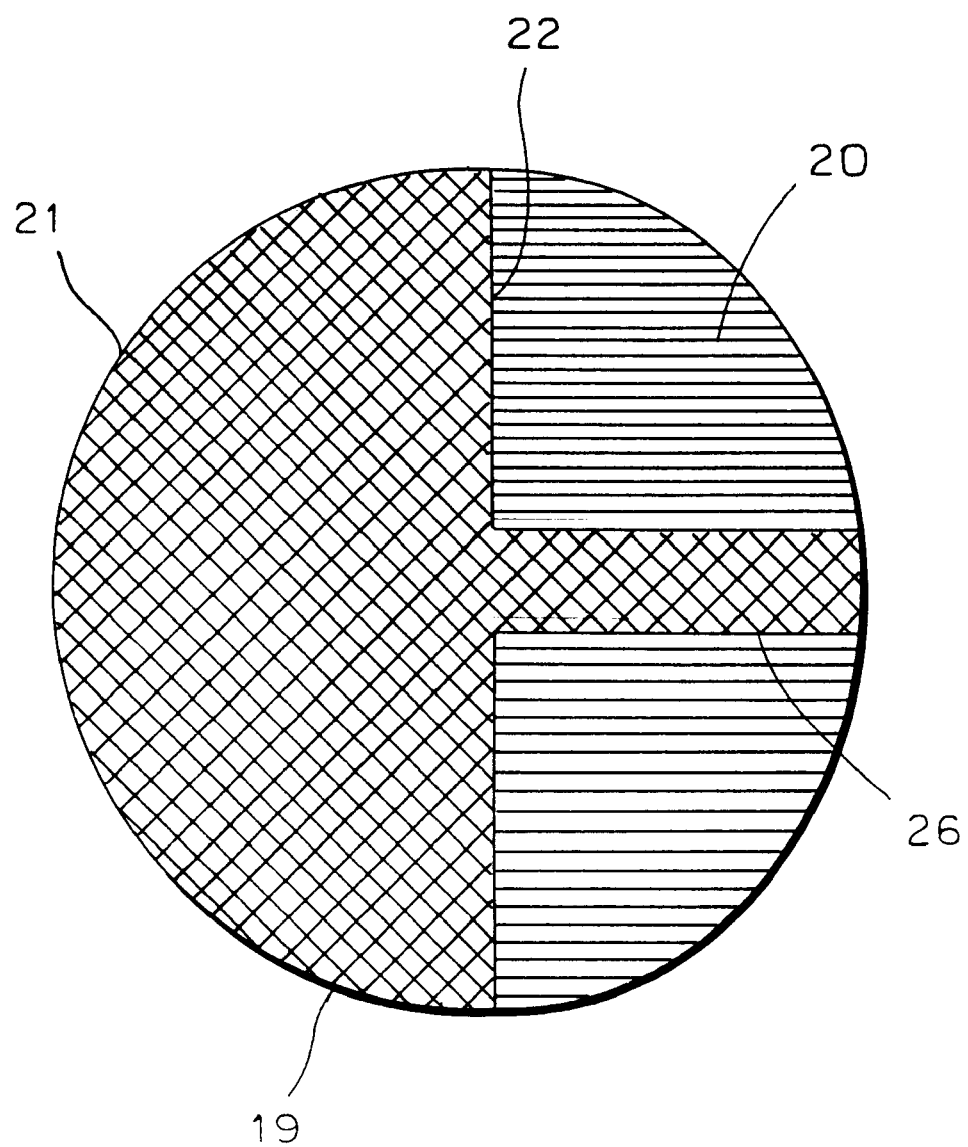
FIG. 5 illustrates a sagittal section of a third preferred embodiment of the invention, in which the prosthesis comprises a homogeneous gel hemisphere and a sponge hemisphere, and in which the sponge hemisphere is strengthened by the presence of a column of gel passing through its centre.

However in this embodiment a column of the gel form of PHEMA (26) passes from the surface of the anterior hemisphere to the centre of the prosthesis. The gel column may extend all the way to the posterior hemisphere, as illustrated in FIG. 5, or may extend only partly through the anterior hemisphere.

The gel column increases the mechanical strength of the anterior hemisphere. When the extraocular muscles are sutured to the implant, the muscles overly the anterior hemisphere, but the sutures are passed through the sponge so that they emerge through the reinforced central area. This reduces the risk of tears occurring in the sponge. Such tears are detrimental, because they may allow the muscles to detach from the implant. However, once healing and tissue ingrowth into the anterior hemisphere has commenced, the muscles do not detach, even though the suture material undergoes biodegradation.

While the gel cylinder provides a stronger anterior anchor area for the sutures, it is to be clearly understood that this modification is optional, and is not required if the strength of the sponge material utilised for the anterior hemisphere is increased.

In all three embodiments the overall diameter of the prosthesis is preferably 14 to 22 mm, but it will be appreciated that this can be adjusted to accommodate the needs of individual patients. In the second embodiment, the outer sponge layer (24) is preferably 2 to 4 mm thick. Again this will depend on the needs of the individual patient.

While the figures illustrate the prostheses as perfect spheres, in both embodiments the surface of the prosthesis may comprise a means such as a point, nipple, hole or groove to permit interlocking with the externally-worn cosmetic shell. In the first preferred embodiment this will be located at the most anterior point of the anterior hemisphere. In the second embodiment, this may be located at any site, and the prosthesis rotated in order to interlock with corresponding means on the cosmetic shell.

Preferably the prosthesis will be soaked in antibiotic solution before use, in order to minimise the risk of infection. The person skilled in the art will be aware that a wide range of antibiotics will be suitable for this purpose, and the choice will depend in part on whether the patient suffers from any allergies to antibiotics. Otherwise the choice is at the discretion of the individual surgeon.

EXAMPLE 5

Manufacturing Process for the Prosthesis

The conditions for polymerisation of the homogeneous gel polymer and the sponge polymer, and for the formation of the interpenetrating polymer network, are generally as described in Australian Patent No. 650156. Briefly, the gel polymer is obtained as a homogeneous hydrogel by bulk polymerisation of HEMA to form a non-porous polymer, and the sponge form of PHEMA is produced by polymerisation of HEMA in the presence of a concentration of water higher than a critical value, usually approximately 45% by weight of the initial monomer mixture, in order to produce a heterogeneous hydrogel with a porosity adjustable between 5 and 80 microns.

In the preferred embodiments of the invention, in the situation where other monomers are to be used in conjunction with HEMA for the production of the sponge polymer it is important that only hydrophobic monomers should be used, since the sponge must be sufficiently strong to prevent tearing or cutting by the sutures used to attach the ocular tissues to the prosthesis.

The crude prosthesis is formed within a mould or moulds of the appropriate size and shape. It is then cut by any suitable method, such as cryolathing, to the desired final size and shape required for the individual patient.

In one preferred example of the process of manufacture of a prosthesis according to the invention, there are three steps involved in the casting procedures, including the optional modification in which a gel cylinder is created within the anterior hemisphere.

a) Casting the Sponge Hemisphere
   Sponge Formulation
   8 g water (Milli-Q purified water)
   2 g 2-hydroxyethyl methacrylate (HEMA) monomer
   17.2 microliters divinyl glycol (DVG) crosslinking agent
   40 microliters 10% w/v ammonium persulphate (APS) solution
   40 microliters tetramethylethylene diamine (TEMED)

Water, HEMA monomer, DVG, and APS are mixed, then TEMED is added to the solution immediately prior to casting, as polymerisation occurs rapidly after addition of this agent. Immediately after addition of the TEMED the solution is placed in a polypropylene tube containing a cryolathe spindle, to a depth sufficient to cover the spindle. In general approximately 7.3 g of solution will suffice. The tube is capped, and left on a level surface for at least two hours to allow polymerisation to take place. After polymerisation is completed, the sponge is rinsed several times with purified water while still in the tube. The spindle is gently removed, rotating it so as to cause minimal damage to the sponge. If a hole is formed in the sponge during withdrawal of the spindle, the preparation must be rejected. The tube containing the sponge is stored in a capped specimen jar or other suitable vessel, together with a small quantity of purified water to prevent dehydration of the sponge.

b) Casting and Lathing the Gel Hemisphere
   Gel Formation
   4.35 g water (Milli-Q purified water)
   9.65 g 2-hydroxyethyl methacrylate (HEMA) monomer
   50.2 microliters ethyleneglycoldimethacrylate (EDMA) crosslinking agent
   214 microliters 10% w/v ammonium persulphate (APS) solution The gel components are mixed, and sufficient of the resulting solution is added to the sponge in the tube, prepared as in Step 1, to fill the tube; generally between 13 and 14 g will suffice. The tube is recapped and replaced in the specimen jar, again containing a small quantity of purified water to prevent dehydration. The jar is placed in an air oven at 50°C. for at least 5 hours to permit polymerisation, then removed and allowed to cool at room temperature. The cap of the tube is removed and a series of vertical incisions (approximately 5 to 8 mm long) are cut around the periphery of the top of the polypropylene cylinder using a scalpel, the number of these cuts being sufficient to enable the polypropylene between them to be easily folded outwards, thus exposing the top 5 to 8 mm of the cast gel cylinder. Insertion of a sharp instrument horizontally into this to portion enables the combined gel/sponge part to be gently extracted from the mould. If the sponge and gel halves of the cylinder separate, the preparation is rejected. Once the gel-sponge cylinder has been removed from the tube, the gel is cut with a scalpel about 12 mm above the gel-sponge interface, and the gel is rounded off around the top in order to facilitate lathing. The gel-sponge cylinder is now ready for its first lathing to convert it from cylindrical to spherical shape. The cylinder is mounted on the lathe spindle, using Tissue-Tek™ in the hole which was created during the initial sponge casting. The mounted gel-sponge is then placed in a freezer at −75° C. for at least one hour, after which it can be cryolathed under a stream of dry ice. The gel hemisphere is cut to the required radius of curvature. Care should be taken not to remove too much material at a time, since this generates lateral stress, which may cause loss of adhesion to the lathe spindle. In addition to cutting the gel hemisphere, at this stage about 20 mm of the sponge is also cut beyond the gel, so that it is the same diameter as the gel hemisphere. However, at this stage no radius is cut on the sponge section. It is strongly preferable to cut the gel hemisphere in a single lathing operation, since the sponge is not very resilient; and consequently if the sponge does not adhere sufficiently to the lathe spindle and relathing is required, it is very difficult to realign it along the axis created during the first lathing. Thus asymmetry is likely to result.

c) Addition of a Gel Reinforcement Through the Sponge Hemisphere, and Lathing the Sponge If a gel reinforcement is desired, as in the third embodiment of the invention described in Example 3, the gel-sponge is thawed and placed into another polypropylene tube with the gel hemisphere facing down. The hole in the sponge is filled with the gel formulation described in Step b) above; about 0.7 g is generally required. The gel is polymerised in an air oven at 50° C., as described in Step b). The tube is removed from the oven, allowed to cool, and then the sponge section is cut laterally about 12 mm from the gel hemisphere.

The preparation is mounted with Tissue-Tek™ on the concave polytetrafluoroethylene disk which is previously mounted using Tissue-Tek™ on to the appropriate lathe spindle. The preparation is frozen at −75°C. as described in Step b), and the sponge hemisphere is cryolathed to yield a spherical orbital implant with equal sized gel and sponge hemispheres, and optionally comprising a gel cylinder within the centre of the sponge hemisphere.

The finished prosthesis is rinsed with purified water, then subjected to continuous hot water flushing for 16 hours, for example in a Soxhlet apparatus, in order to remove unreacted monomers. On removal from the Soxhlet apparatus, the prosthesis is placed into sterile balanced salt solution and is autoclaved, after which it can be stored until required for implantation. The prosthesis may optionally be soaked in a variety of therapeutic agents, such as anti-inflammatory agents, antibiotics or growth factors, prior to implantation.

Figure 6:
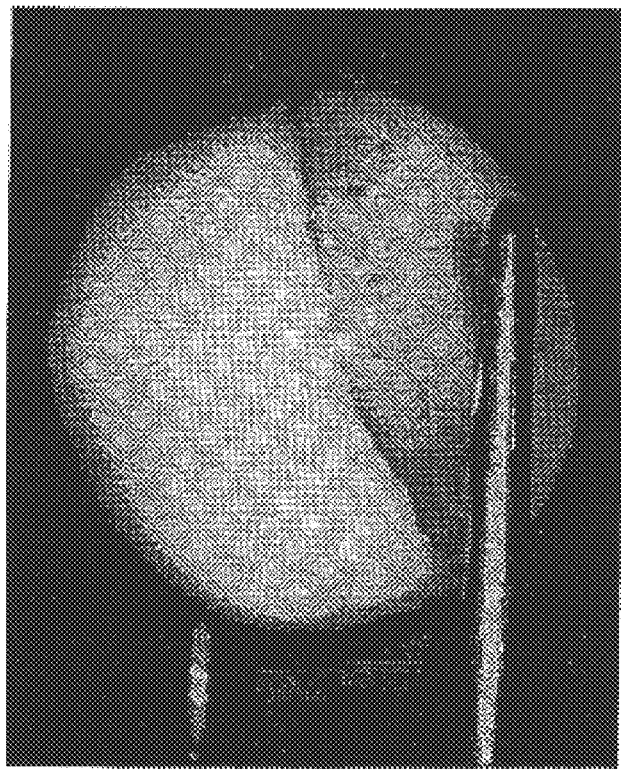
FIG. 6 is a photograph showing an implant according to the first preferred embodiment of the invention.

A photograph of a finished prosthesis according to the invention is shown in FIG. 6.

EXAMPLE 6

Surgical Implantation of the Prosthesis

The surgical technique for implantation is the same for both embodiments of the invention.

Following dissection of the conjunctiva, Tenon's capsule and the extrinsic muscles, and removal of the eyeball, the prosthesis is placed into the eye socket, the rectus muscles are sutured anteriorly to the sponge, and Tenon's capsule is closed anteriorly by a purse-string suture. Finally the conjunctiva is closed with a continuous suture. Once the incisions have healed, an external cosmetic shell is placed in position over the anterior surface of the prosthesis under the eyelids.

EXAMPLE 7

Animal Trial of the Socket Prosthesis

A pilot study has been performed in which prototype prostheses according to the first preferred embodiment have been implanted within the eye sockets of rabbits which have undergone enucleation. To date, a total of twenty implantations have been performed. All animal studies have been carried out in accordance with the Australian code of practice for the care and use of animals for scientific purposes.

Figure 7:
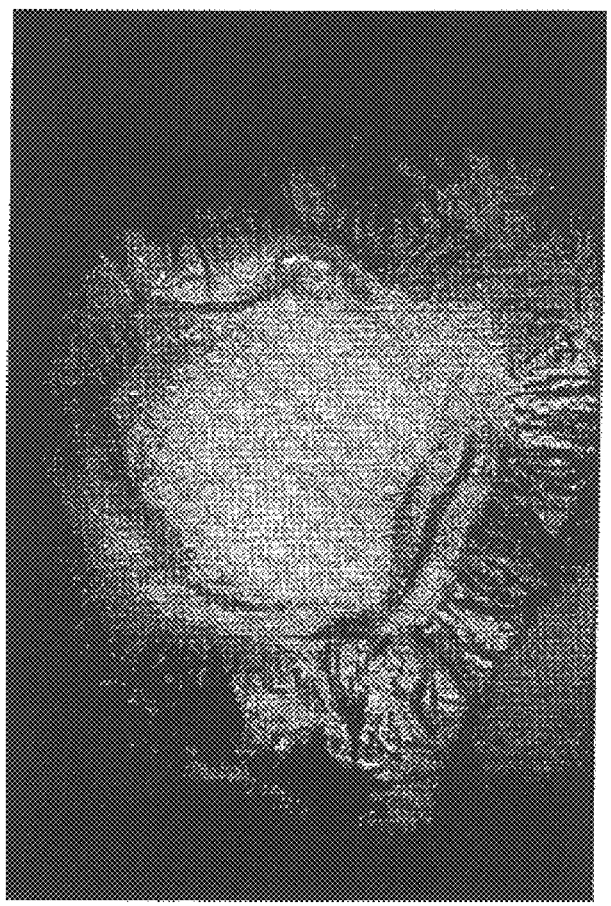
FIG. 7 shows the appearance of an implant according to the first embodiment at six months after implantation into a rabbit, showing the thick, continuous conjunctival layer.

The surgical technique is as described above in Example 6, during which the extraocular muscles are sutured directly on to the prosthesis. The prostheses in these cases were not soaked in antibiotics before use, but per-operative antibiotics were given. The period of post-operative follow-up now ranges up to 18 months, and there have been no cases of extrusion. FIG. 7 illustrates the appearance of the prosthesis at six months after implantation, and shows that the implant is covered with a thick, continuous conjunctival layer. Although eye movements in a rabbit are hard to assess, in the rabbits which were fitted with a cosmetic shell, "eye" movement appears natural, and the general appearance was very satisfactory.

In one rabbit, the sutures holding the muscles to the implant tore out of the sponge in the early post-operative period, allowing rotation of the implant: deep to the conjunctival flap. This caused the gel hemisphere to underlie the conjunctiva, and self-inflicted trauma to the conjunctiva over the non-vascularised, relatively unyielding gel caused the gel to tear, allowing infection to occur. This necessitated removal of the implant. This led us to adopt the reinforced prosthesis of the third embodiment of the invention described in Example 3, which reduces the risk of suture tearing and implant rotation. Since adoption of this embodiment no similar complications have occurred.

Figure 8:
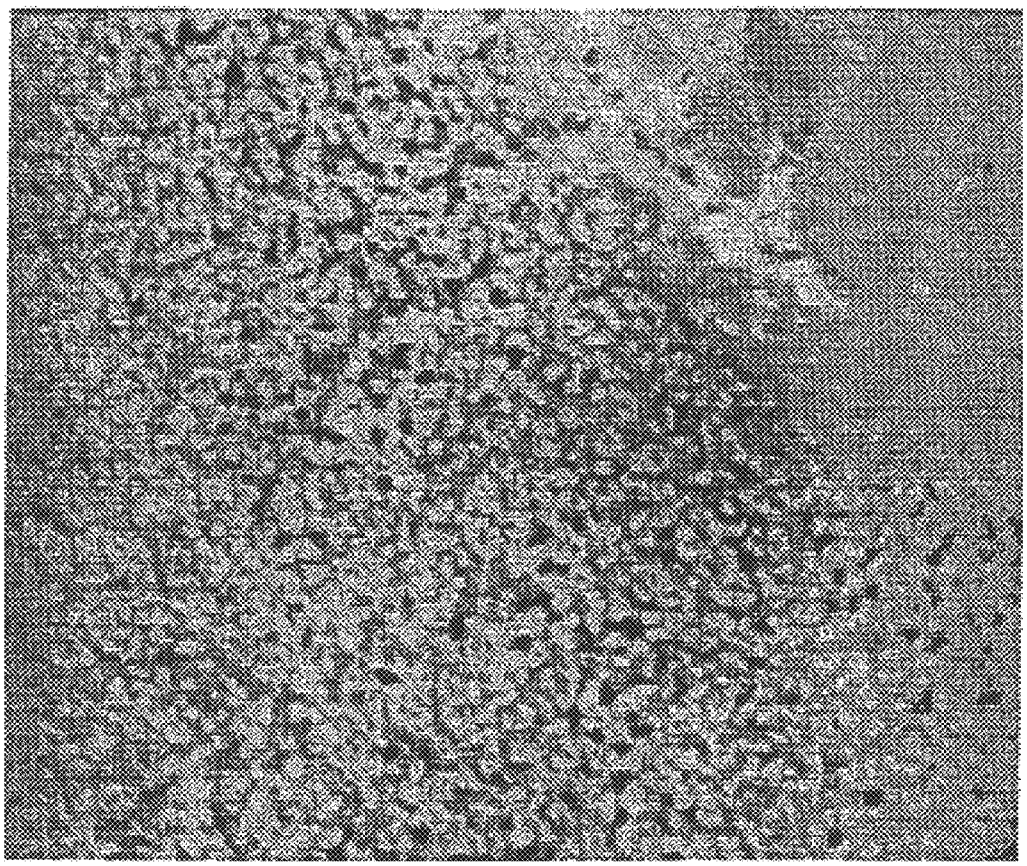
FIG. 8 is a histological section of the anterior (sponge) half of an implant according to the first embodiment of the invention, showing extensive infiltration of tissue into the implant.

One rabbit was euthanased four months after implantation for reasons unrelated to the surgery, and histological examination of the implant from this animal confirmed that good tissue integration had occurred within the anterior sponge hemisphere, with ingrowth of fibroblasts and neovascularisation, and that no adhesions to the posterior hemisphere had occurred. The extensive biocolonisation is illustrated in FIG. 8, which shows a haematoxylin and eosin-stained section of the anterior sponge half of the implant. More detailed histological studies of the healing process are being performed, and are being correlated with magnetic resonance imaging studies.

The prosthesis of the invention can be produced at relatively low cost, making orbital prostheses available to patients who live in areas where the hydroxyapatite implants of the prior art are prohibitively expensive, or where eye banks for provision of donor sclera are not available. The polymer sponge used in the invention provides a cushioning effect, making mechanical erosion of the prosthesis less likely. Furthermore, the porosity of the sponge permits cellular ingrowth, providing a firmer attachment of the surrounding tissues and lowering the risk of extrusion. The ability of the prosthesis of the invention to be soaked in antibiotic solution and to take up such antibiotic prior to implantation reduces the risk of infection. The ability of the invention to provide a means of interlocking with the external cosmetic shell without breaching the conjunctiva provides a significant margin of safety over hydroxyapatite implants, in many forms of which it is necessary to breach the conjunctival covering tissue by a peg placed into the prosthesis in order to couple it to the cosmetic shell.

It is considered that the implant of the invention represents a significant improvement over the prior art, and has characteristics which approach the criteria of the ideal implant as set out by Soll (1982).

It will be apparent to the person skilled in the art that while the invention has been described in some detail for the purposes of clarity and understanding, various modifications and alterations to the embodiments and methods described herein may be made without departing from the scope of the inventive concept disclosed in this specification.

References cited herein are listed on the following pages, and are incorporated herein by this reference.

REFERENCES

Berry, F. D. "A Modified Tissue Expander for Socket Enlargement in Clinical Anophthalmos" Ophthalmic Plast. Reconstr. Surg., 1991 7 41–47

Borodic, G. E., Townsend, D. J. and Beyer-Machule, C. K. "Dermis Fat Graft in Eviscerated Sockets" Ophthalmic Plast. Reconstr. Surg., 1989 5 144–149

Buettner, H. and Bartley, G. B. "Tissue Breakdown and Exposure Associated with Orbital Hydroxyapatite Implants". Am. J. Ophthalmol., 1992 113 669–673

Chirila, T. V., Vijayasekaran, S., Horne, R. Chen Y-C, Dalton, P. D. Constable, I. J. and Crawford, G. J. "Interpenetrating Polymer Network (IPN) as a Permanent Joint Between the Elements of a New Type of Artificial Cornea" J. Biomed. Mat. Res., 1994 28 745–753

Dutton, J. J. "Coralline Hydroxyapatite as an Ocular Implant" Ophthalmology, 1991 98 371–377

Girard, L. J., Eguez, I. Soper, J. W., Soper, M. Esnaola, N. and Homsy C. A. "Buried Quasi-Integrated Enucleation Implant of Proplast II" Ophthalmol. Plast. Reconstr. Surg., 1990 6 141–143

Girard, L. J., Esnaola, N. and Sagahon, E. "Evisceration Implant of Proplast II" Ophthalmic Plast. Reconstr. Surg., 1990 6 139–140

Goldberg, R. A., Dresner, S. C., Braslow, R. A. Kossovsky, N. and Legmann, A. "Animal Model of Porous Polyethylene Orbital Implants" Ophthalmic Plast. Reconstr. Surg., 1994 10 104–109

Kennedy, R. E. "Growth Retardation and Volume Determinations of the Anophthalmic Orbit" Am. J. Ophthalmol., 1973 76 294–302

Lang, W. "On the Insertion of Artificial Globes into Tenon's Capsule After Excising the Eye" Trans. Ophthalmol. Soc. U.K., 1887 7 286–291

Legeais, J-M., Rossi, C., Renard, G., Salvoldelli, D'Hermies, F. and Pouliquen, Y. J. "A New Fluorocarbon for Keratoprosthesis" Cornea, 1992 11 538–545

McNab, A. "Hydroxyapatite Orbital Implants" Aust. NZ J. Ophthalmol, 1995 23 117–123

Migliori, M. E. and Putterman, A. M. "The Domed Dermis-Fat Graft Orbital Implant" Ophthalmic Plast. Reconstr. Surg., 1991 7 23–30

Molgat, Y. M., Hurwitz, J. J. and Webb, M. C. F. "Buccal Mucous Membrane-Fat Graft in the Management of the Contracted Socket" Ophthalmic Plast. Reconstr. Surg., 1993 9 267–272

Mules, P. H. "Evisceration of the Globe, with Artificial Vitreous" Trans. Ophthalmol. Soc. U.K., 1884 5 200–206

Neuhaus, R. W., Greider, B. and Baylis, H. I. "Enucleation with Implantation of a Proplast Sphere" Ophthalmology, 1984 91 494–496

Nunery, W. R., Cepela, M. A., Heinz, G. W., Zale, D. and Martin, R. T. "Extrusion Rate of Silicone Anophthalmic Socket Implants" Ophthalmic Plast. Reconstr. Surg., 1993 9 90–95

Nunery, W. R., Heinz, G. W., Bonnin, J. M., Martin, R. T. and Cepela, M. A. "Exposure Rate of Hydroxyapatite Spheres in the Anophthalmic Socket: Histopathologic Correlation and Comparison with Silicone Sphere Implants" Ophthalmic Plast. Reconstr. Surg., 1993 9 96–104

Rosner, M., Edward, D. P. and TSo, M. O. M. "Foreign Body Giant Cell Reaction to the Hydroxyapatite Orbital Implant" Arch. Ophthalmol., 1992 110 173–174

Rubin, P. A. D., Popham, J. K., Bilyk, J. R. and Shore, J. W. "Comparison of Fibrovascular Ingrowth into Hydroxyapatite and Porous Polyethylene Orbital Implants" Ophthalmic Plast. Reconstr. Surg., 1994 10 96–103

Shields, C. L., Shields, J. A. and DePotter, P. "Hydroxyapatite Orbital Implant After Enucleation" AM. J. Ophthalmol., 1992 110 333–338

Shields, C. L., Shields, J. A. and De Potter, P. "Hydroxyapatite Orbital Implant After Enucleation for Intraocular Tumours" Int. Ophthalmol. Clin., 1993 33 83–92

Shields, C. L., Shields, J. A., De Potter P. and Singh, A. D. "Problems with the Hydroxyapatite Orbital Implant: Experience with 250 Consecutive Cases" Br. J. Ophthalmol., 1994 78 702–706

Shields, C. L., Shields, J. A., Eagle, R. C. and De Potter, P. "Histopathologic Evidence of Fibrovascular Ingrowth Four Weeks After Placement of the Hydroxyapatite Orbital Implant" Am. J. Opthalmol., 1991 111 363–366

Smith, B. R., Beyer-Machule, C. K., Cheng, H-M. and Pitts, W. C. "Fate of Primary Orbital Dermis-Fat Grafts in Guinea Pigs" Ophthalmic Plast. Reconstr. Surg., 1988 4 193–201

Smith, B. and Petrelli, R. "Dermis-Fat Graft as a Moveable Implant Within the Muscle Cone" Am. J. Ophthalmol., 1978 85. 62–66

Soll, D. B. "Donor Sclera in Enucleation Surgery" Arch. Ophthalmol., 1974 92 494–495

Soll, D. "The Anophthalmic Socket" Ophthalmology, 1982 89 407–423

What is claimed is:

1. An ocular socket prosthesis having an anterior surface and comprising a hydrogel consisting essentially of a biocompatible hydrophilic polymer which polymer is in both its homogenous gel form and in its sponge form, and the two forms are chemically joined at their interface via an interpenetrating polymer network (IPN), or are joined by an adhesive on to which tissues can be directly sutured.

2. An ocular socket prosthesis having an anterior surface and comprising a hydrogel consisting essentially of a biocompatible hydrophilic polymer on to which tissues can be directly sutured, wherein the polymer is predominantly or entirely in its sponge form.

3. A prosthesis according to claim 1, in which the polymer is poly(2-hydroxyethyl methacrylate) (PHEMA).

4. A prosthesis according to claim 1, in which the polymer is a copolymer of 2-hydroxyethyl methacrylate (HEMA) and a hydrophilic or hydrophobic monomer selected from the group consisting of hydroxylated methacrylates and acrylates, acrylamide derivatives and N-vinylpyrrolidone and combinations thereof; hydrophobic methacrylates and acrylates; and other hydrophobic monomers.

5. A prosthesis according to claim 1, wherein the anterior surface of the prosthesis additionally carries connecting means adapted to cooperate with corresponding receiving means on an externally-worn cosmetic shell.

6. A method of producing an ocular prosthesis selected according to claim 1, comprising the steps of:
  (a) forming a hydrogel sponge portion in a mould, and
  (b) subsequently forming a hydrogel portion in the same mould,
    under conditions such that during step (b) a monomer mixture of the hydrogel firstly penetrates to some extent into a pre-existing polymer matrix left over from the hydrogel sponge and subsequently undergoes polymerisation, so as to form an interpenetrating polymer network along a boundary between the two portions.

7. A method according to claim 6, in which the prosthesis is impregnated with collagen prior to implantation.

8. A method of providing an ocular socket prosthesis, comprising the step of surgical implantation of a prosthesis according to claim 1 into the enucleated ocular socket of a subject in need of such treatment.

9. A method according to claim 8, in which the rectus muscles are sutured anteriorly to the sponge.

10. A method according to claim 8, in which the prosthesis is soaked in antibiotic solution prior to implantation.

11. A method according to claim 8 in which an external cosmetic shell is placed over the anterior surface of the prosthesis after surgical implantation.

12. An ocular socket prosthesis having an anterior surface and comprising a hydrogel consisting essentially of a biocompatible hydrophilic polymer which polymer is in both its homogenous gel form and its sponge form on to which tissues can be directly sutured,
  wherein the prosthesis is generally spherical, and comprises a posterior hemisphere consisting essentially of the gel form of the polymer and wherein said anterior surface comprises an anterior hemisphere consisting essentially of the sponge form of the polymer, said anterior and posterior hemispheres being permanently joined at their interface by an IPN or by an adhesive.

13. A prosthesis according to claim 12, wherein the anterior hemisphere is strengthened by a column of the gel form of the polymer, which extends from the surface of the anterior hemisphere towards the centre of the prosthesis, and wherein the gel column optionally extends to meet the posterior hemisphere.

14. An ocular socket prosthesis having an anterior surface and comprising a hydrogel consisting essentially of a biocompatible hydrophilic polymer which polymer is in both its homogenous gel form and its sponge form on to which tissues can be directly sutured,
  wherein the prosthesis is generally spherical, and comprises two generally concentric regions, with a generally spherical central core consisting essentially of the homogenous gel form of the polymer surrounded by a layer of the sponge form of the polymer, the core and the outer layer being permanently joined by an IPN or by an adhesive.

* * * * *